(12) United States Patent
Takakura et al.

(10) Patent No.: US 9,151,899 B2
(45) Date of Patent: Oct. 6, 2015

(54) OPTICAL FIBER HEAD

(71) Applicant: OMRON CORPORATION, Kyoto (JP)

(72) Inventors: Takeshi Takakura, Kyoto (JP);
Atsunobu Fujii, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 0 days.

(21) Appl. No.: 14/028,895

(22) Filed: Sep. 17, 2013

(65) Prior Publication Data

US 2014/0086529 A1 Mar. 27, 2014

(30) Foreign Application Priority Data

Sep. 27, 2012 (JP) ................................ 2012-213778

(51) Int. Cl.
| | | |
|---|---|---|
| *G02B 6/36* | (2006.01) | |
| *G02B 6/38* | (2006.01) | |
| *G02B 6/32* | (2006.01) | |
| *G01N 21/47* | (2006.01) | |

(52) U.S. Cl.
CPC ................ *G02B 6/32* (2013.01); *G01N 21/474* (2013.01); *G02B 6/322* (2013.01); *G02B 6/3853* (2013.01)

(58) Field of Classification Search
CPC ....... G02B 6/32; G02B 6/3853; G01N 21/474
USPC .......... 385/33, 61, 62, 74, 79, 81, 84
See application file for complete search history.

(56) References Cited

U.S. PATENT DOCUMENTS

| | | | |
|---|---|---|---|
| 4,753,510 A | 6/1988 | Sezerman | |
| 4,776,663 A * | 10/1988 | Malinge et al. | 385/79 |
| 4,810,053 A * | 3/1989 | Woith | 385/79 |
| 5,243,681 A | 9/1993 | Bowen et al. | |
| 5,511,139 A * | 4/1996 | Nodfelt | 385/60 |
| 8,616,781 B2 * | 12/2013 | Knapp | 385/61 |
| 2012/0155807 A1 | 6/2012 | Knapp | |

FOREIGN PATENT DOCUMENTS

| | | | |
|---|---|---|---|
| FR | 2820789 | * 12/2000 | F16B 4/00 |
| JP | 06-160668 | 6/1994 | |
| JP | 6-160668 | 6/1994 | |

OTHER PUBLICATIONS

Search report from E.P.O., mail date is Jan. 7, 2014.

* cited by examiner

*Primary Examiner* — Robert Tavlykaev

(74) *Attorney, Agent, or Firm* — Greenblum & Bernstein P.L.C.

(57) ABSTRACT

This embodiment provides an optical fiber head in which a lens can reliably be fixed to a case body by a simple configuration, and therefore the optical fiber head can easily be produced at low cost. The optical fiber head includes a light projecting fiber, a light projecting lens, and a case body accommodating and holding the light projecting fiber and the light projecting lens. A blocking unit in which an opening is formed, a light projecting lens inserting hole, and an optical fiber inserting hole are provided in the case body. The light projecting fiber is fixed to the case body while a leading end surface of the light projecting fiber abuts a rear end surface of the light projecting lens, so that the light projecting lens is fixed to the case body by being sandwiched between the blocking unit and the light projecting fiber in an axial direction.

12 Claims, 8 Drawing Sheets

OPTICAL FIBER HEAD

CROSS REFERENCE TO RELATED APPLICATIONS

This application claims priority to Japanese Patent Application No. 2012-213778 filed on Sep. 27, 2012, the entire contents of which are incorporated by reference herein.

FIELD

Disclosed herein is an optical fiber head in which a leading end portion of an optical fiber and a lens are held by a case body, particularly to an optical fiber head that can suitably be used as a head of an optical fiber type photoelectric sensor.

BACKGROUND

The optical fiber head properly controls a ray of light exiting from or being incident on a leading end surface of the optical fiber using a lens. In the optical fiber head, the leading end portion of the optical fiber and the lens are held by a case body, so that the leading end portion of the optical fiber and a rear end surface of the lens are disposed so as to be opposed to each other.

Conventionally, the lens is generally fixed to the case body by press-fitting or bonding. For example, Japanese Unexamined Patent Publication No. 6-160668 discloses the optical fiber head in which the lens is fixed to the case body by the press-fitting.

However, in the case that the lens is fixed to the case body by the press-fitting, it is necessary to strictly manage dimensional accuracy of the lens or the case body, and unfortunately production cost increases. Additionally, in the case that the lens is fixed to the case body by the press-fitting, a stress is applied to an outer circumferential surface, which serves as a reflection surface, of the lens, and there is a risk of having no small adverse effect on an optical property.

On the other hand, in the case that the lens is fixed to the case body by the bonding, it is necessary to perform work to apply and cure a bonding agent, which results in a problem in that assembly work becomes troublesome to increase the production cost. In order to sufficiently ensure a holding force of the case body to the lens, it is necessary to strictly manage an application amount or a curing condition of the bonding agent, which also increases the production cost.

SUMMARY

The embodiment has been devised to solve the problems described above, and an object thereof is to provide an optical fiber head, in which the lens can reliably be fixed to the case body by a simple configuration, and therefore the optical fiber head can easily be produced at low cost.

In accordance with a first aspect of the embodiment, an optical fiber head includes: an elongated, columnar optical fiber including a leading end surface in a leading end portion in an axial direction, light exiting from and being incident on the leading end surface; a substantially columnar lens disposed so as to be opposed to the leading end surface of the optical fiber; and a case body including a front end and a rear end in the axial direction, the leading end portion of the optical fiber and the lens being accommodated in the case body, the optical fiber being drawn from the rear end of the case body. In the optical fiber head, a blocking unit, a lens inserting hole, and an optical fiber inserting hole are sequentially provided in the case body from the front end to the rear end, an opening through which the light is projected or received being formed in the blocking unit, the lens being inserted in the lens inserting hole, the leading end portion of the optical fiber being inserted in the optical fiber inserting hole. An inner diameter of the lens inserting hole is larger than an diameter of the opening and is smaller than an inner diameter of the optical fiber inserting hole. A length in the axial direction of the lens is longer than a length in the axial direction of the lens inserting hole. In the optical fiber head according to the first aspect of the present invention, the leading end portion of the optical fiber is fixed to the case body while the leading end surface of the optical fiber abuts on a rear end surface of the lens by inserting the lens in the lens inserting hole, and the leading end portion of the optical fiber in the optical fiber inserting hole, so that the lens is fixed to the case body by being sandwiched between the blocking unit and the optical fiber in the axial direction.

In the optical fiber head of the first aspect of the embodiment, preferably a diameter in the leading end portion of the optical fiber is larger than a diameter of the lens.

In the optical fiber head of the first aspect of the embodiment, preferably the leading end portion of the optical fiber includes: a core wire including a core and a clad; and a coating material coating the core wire.

In the optical fiber head of the first aspect of the embodiment, preferably the leading end portion of the optical fiber is fixed to the case body by crimping in which a diameter of part of the case body is radially reduced.

In accordance with a second aspect of the embodiment, an optical fiber head includes: an elongated, columnar light projecting fiber including a leading end surface in a leading end portion in an axial direction, light exiting from the leading end surface; an elongated, columnar light receiving fiber including a leading end surface in a leading end portion in an axial direction, the light being incident on the leading end surface; a substantially columnar light projecting lens disposed so as to be opposed to the leading end surface of the light projecting fiber; a substantially columnar light receiving lens disposed so as to be opposed to the leading end surface of the light receiving fiber; and a case body including a front end and a rear end in the axial direction, the leading end portion of the light projecting fiber, the leading end portion of the light receiving fiber, the light projecting lens, and the light receiving lens being accommodated in the case body, the light projecting fiber and the light receiving fiber being drawn from the rear end of the case body. In the optical fiber head, a blocking unit, lens inserting holes, and optical fiber inserting holes are sequentially provided in the case body from the front end to the rear end, a light projecting opening through which the light is projected and a light receiving opening through which the light is received being formed in the blocking unit, the light projecting lens and the light receiving lens being inserted in the lens inserting holes, the leading end portion of the light projecting fiber and the leading end portion of the light receiving fiber being inserted in the optical fiber inserting hole. The case body includes a partition configured to partition a light projecting lens inserting hole and a light receiving lens inserting hole of the lens inserting holes, the light projecting lens being inserted in light projecting lens inserting hole, the light receiving lens being inserted in the light receiving lens inserting hole. An inner diameter of the light projecting lens inserting hole is larger than a diameter of the light projecting opening, and is smaller than an inner diameter of the light projecting fiber inserting hole, which is a hole in which the light projecting fiber is inserted in the optical fiber inserting holes. An inner diameter of the light receiving lens inserting hole is larger than a diameter of the light receiving opening, and is smaller than an inner diameter of the light receiving fiber inserting hole, which is a hole in which the light receiving fiber is inserted in the optical fiber inserting holes. A length in the axial direction of the light projecting lens is longer than a length in the axial direction of the light projecting lens inserting hole, a length in the axial direction of the light receiving lens is longer than a length in the axial direction of the light receiving lens inserting hole. In the optical fiber head of the second aspect of the present invention, the leading end portion of the light projecting fiber and the leading end portion of the light receiving fiber are fixed to the case body while the leading end surface of the light projecting fiber and the leading end surface of the light receiving fiber respectively abut on a rear end surface of the light projecting lens and a rear end surface of the light receiving lens by inserting the light projecting lens in the light projecting lens inserting hole, the leading end portion of the light projecting fiber in the light projecting fiber inserting hole, the light receiving lens in the light receiving lens inserting hole, and the leading end portion of the light receiving fiber in the light receiving fiber inserting hole, so that the light projecting lens is sandwiched between the blocking unit and the light projecting fiber in the axial direction and the light receiving lens is sandwiched between the blocking unit and the light receiving fiber in the axial direction, and the light projecting lens and the light receiving lens are fixed to the case body.

In the optical fiber head of the second aspect of the embodiment, preferably a diameter in the leading end portion of the light projecting fiber is larger than a diameter of the light projecting lens, and a diameter in the leading end portion of the light receiving fiber is larger than a diameter of the light receiving lens.

In the optical fiber head of the second aspect of the embodiment, preferably each of the leading end portions of the light projecting fiber and the light receiving fiber includes: a core wire including a core and a clad; and a coating material coating the core wire.

In the optical fiber head of the second aspect of the embodiment, preferably a partition wall projects from the rear end surface of the partition so as to reach a gap between the light projecting fiber and the light receiving fiber.

In the optical fiber head of the second aspect of the embodiment, preferably the leading end portion of the light projecting fiber and the leading end portion of the light receiving fiber are fixed to the case body by crimping in which a diameter of part of the case body is radially reduced.

Accordingly, the embodiment can provide an optical fiber head in which the lens can reliably be fixed to the case body by the simple configuration, and therefore the optical fiber head can easily be produced at low cost.

DETAILED DESCRIPTION

Hereinafter, embodiments of the present invention will be described in detail with reference to the drawings. In the following descriptions of the embodiments, the identical or common component is designated by the identical numeral, and the overlapping description is not repeated.

First Embodiment

Figure 1:
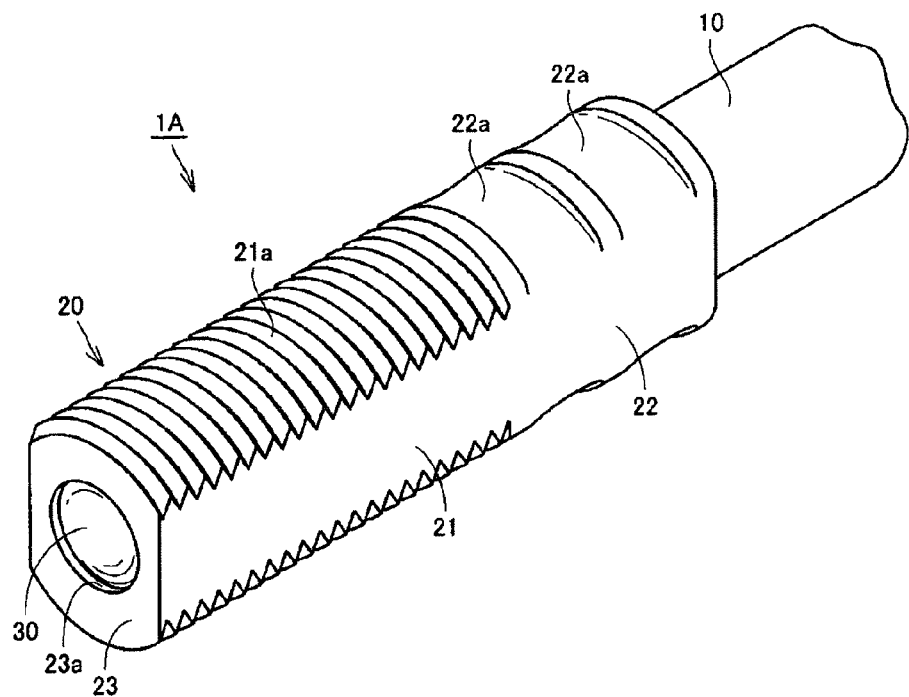
FIG. 1 is a perspective view of an optical fiber head according to a first embodiment of the present invention.
Figure 2:
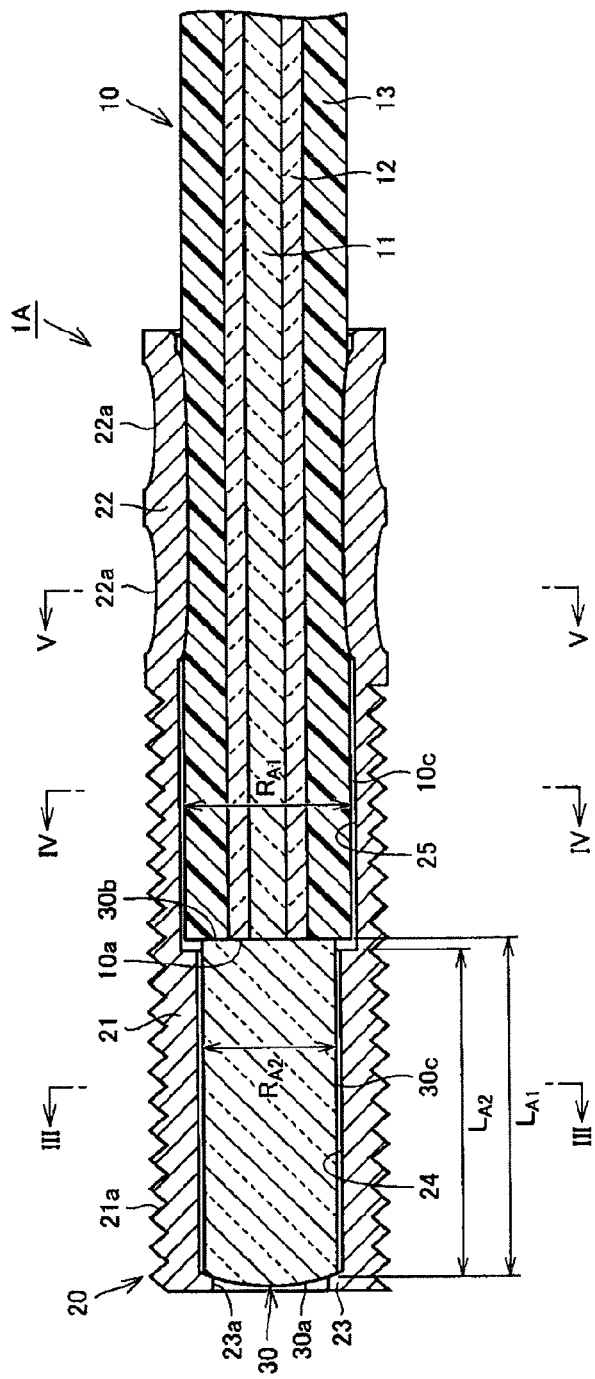
FIG. 2 is a sectional view of the optical fiber head in FIG. 1.
Figure 3:
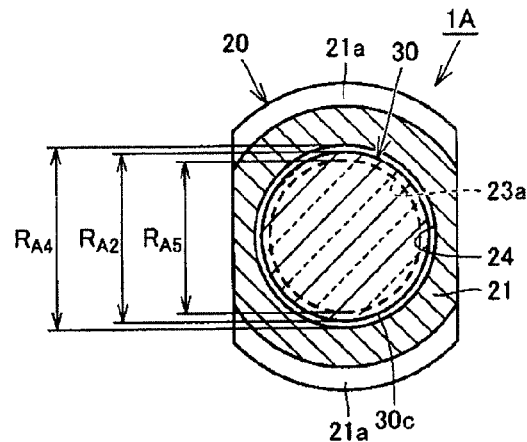
FIG. 3 is a sectional view taken along line III-Ill of FIG. 2.
Figure 4:
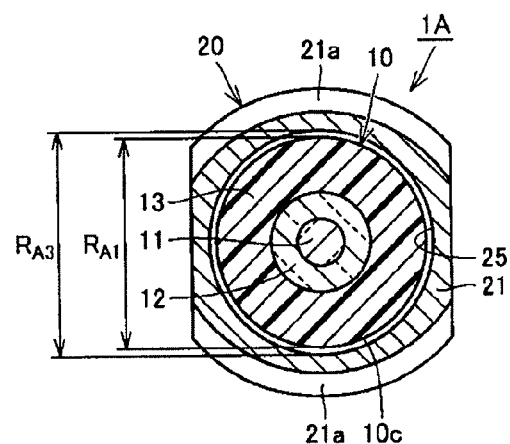
FIG. 4 is a sectional view taken along line IV-IV of FIG. 2.
Figure 5:
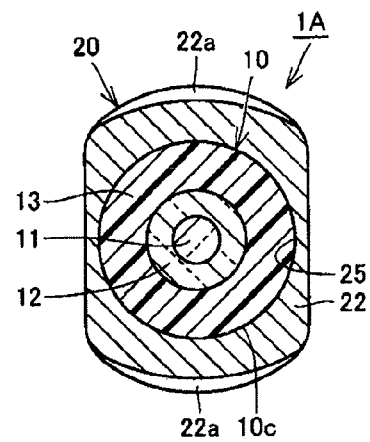
FIG. 5 is a sectional view taken along line V-V of FIG. 2.

FIG. 1 is a perspective view of an optical fiber head according to a first embodiment of the present invention, and FIG. 2 is a sectional view of the optical fiber head in FIG. 1. FIGS. 3 to 5 are sectional views taken along lines IV-IV, and V-V of FIG. 2, respectively. A configuration of an optical fiber head 1A of the first embodiment will be described with reference to FIGS. 1 to 5. The optical fiber head 1A of the first embodiment is configured as a light projecting head for a transmission optical fiber type photoelectric sensor.

As illustrated in FIGS. 1 to 5, the optical fiber head 1A of the first embodiment includes a light projecting fiber 10, a case body 20, and a light projecting lens 30.

The light projecting fiber 10 transmits light and performs light projection to the outside. The light projecting fiber 10 is configured by an elongated, columnar member that includes a core wire including a core 11 and a clad 12 and a coating material 13 coating the core wire. The core 11 and the clad 12 are made of a light transmissive material, and the coating material 13 is made of a light-blocking material.

One of a POF (Plastic Optical Fiber) and a GOF (Glass Optical Fiber) can be used as the light projecting fiber 10, more preferably the POF can be used. As to a specific material for the core 11 and the clad 12, resin material typified by acrylic resins such as a polymethylmethacrylate resin or fluorine resins can be used for the POF, general glass materials can be used for the GOF. For example, resin materials typified by polyvinyl chloride can be used as the coating material 13.

The light projecting fiber 10 includes a leading end surface 10a, from which the light exits, in a leading end portion in an axial direction thereof. In the leading end portion of the light projecting fiber 10, the core wire including the core 11 and the clad 12 is not exposed, but the core wire is coated with the coating material 13.

The case body 20 holds the leading end portion of the light projecting fiber 10 and the light projecting lens 30, and has a hollow, substantially cylindrical shape. For example, the case body 20 is made of a metallic material such as zinc alloy, stainless steel, and steel.

The case body 20 includes a main body 21 located on a front end (a left end portion in FIG. 2) side in the axial direction, a fixing unit 22 located on a rear end (a right end portion in FIG. 2) side in the axial direction, and a blocking unit 23 located at the front end.

A light projecting lens inserting hole 24 in which the light projecting lens 30 is inserted is made in the main body 21 on the front end side, and a light projecting fiber inserting hole 25 in which the leading end portion of the light projecting fiber 10 is inserted is made in the main body 21 on the rear end side and in the fixing unit 22. A light projecting opening 23a is provided in the blocking unit 23 so as to pierce the blocking unit 23 in the axial direction. The light projecting opening 23a projects the light of which a ray is controlled by the light projecting lens 30 toward the outside of the optical fiber head 1A.

The light projecting opening 23a, the light projecting lens inserting hole 24, and the light projecting fiber inserting hole 25 pierce the case body 20 so as to communicate with one another. Therefore, the blocking unit 23 in which the light projecting opening 23a is provided, the light projecting lens inserting hole 24 in which the light projecting lens 30 is inserted, and the light projecting fiber inserting hole 25 in which the leading end portion of the light projecting fiber 10 is inserted are sequentially provided in the case body 20 from the front end to the rear end.

An external thread 21a is provided on an outer circumferential surface of the main body 21. The external thread 21a is used to mount the optical fiber head 1A. On the other hand, a crimping portion 22a is provided at a predetermined position in the axial direction of the fixing unit 22. The crimping portion 22a holds the light projecting fiber 10 inserted in the case body 20.

The light projecting lens 30 controls the ray of the light exiting from the leading end surface 10a of the light projecting fiber 10. The light projecting lens 30 is made of a light transmissive material. For example, the light projecting lens 30 is configured by an injection molding product made of a resin material typified by an acrylic resin.

The light projecting lens 30 has a substantially columnar shape, a front end surface 30a (the left end surface in FIG. 2) of the light projecting lens 30 is configured by a convex lens surface, and a rear end surface 30b (the right end surface in FIG. 2) of the light projecting lens 30 is configured by a planar surface.

A glass lens can be used as the light projecting lens 30 in addition to the resin lens of the injection molding product.

The leading end portion of the light projecting fiber 10 and the light projecting lens 30 are accommodated in the light projecting fiber inserting hole 25 and the light projecting lens inserting hole 24, which are made in the case body 20, respectively. More particularly, the leading end portion of the light projecting fiber 10 is disposed in the light projecting fiber inserting hole 25 provided on the rear end side of the case body 20, and the light projecting lens 30 is mainly disposed in the light projecting lens inserting hole 24 provided on the front end side of the case body 20. A portion except the leading end portion of the light projecting fiber 10 is externally drawn from the rear end of the case body 20.

Therefore, the leading end surface 10a of the light projecting fiber 10 and the rear end surface 30b of the light projecting lens 30 are disposed in the case body 20 while opposed to each other, and the leading end surface 10a of the light projecting fiber 10 and the rear end surface 30b of the light projecting lens 30 abut on each other in the case body 20.

As described above, the leading end portion of the light projecting fiber 10 is held by the crimping portion 22a provided in the fixing unit 22 of the case body 20. The fixing unit 22 is plastically deformed such that a diameter of part of the fixing unit 22 is reduced in the axial direction, thereby forming the crimping portion 22a. The light projecting fiber 10 disposed in the case body 20 is radially nipped by the crimping portion 22a in which the diameter is reduced.

More particularly, as described above, because the core wire including the core 11 and the clad 12 is coated with the coating material 13 in the leading end portion of the light projecting fiber 10 held by the crimping portion 22a, the coating material 13 having proper elasticity is pressed and deformed by the crimping portion 22a in which the diameter is reduced, and the crimping portion 22a bites into an outer circumferential surface 10c of the coating material 13 to rigidly fix the light projecting fiber 10. The coating material 13 having the elasticity is located between the crimping portion 22a and the core wire to reduce the deformation of the core wire, which allows an optical property of the light projecting fiber 10 to be prevented from being degraded due to the crimping.

After the crimping, the light projecting fiber 10 may strongly be held by the case body 20 by previously providing an irregular shape such as an internal thread shape to an inner circumferential surface of the case body 20 at a portion in which the crimping portion 22a is located.

On the other hand, the light projecting lens 30 is fixed to the case body 20 by sandwiching the light projecting lens 30 between the blocking unit 23 of the case body 20 and the light projecting fiber 10 in the axial direction. The light projecting lens 30 is not press-fitted in the light projecting lens inserting hole 24, but the light projecting lens 30 is disposed in the light projecting lens inserting hole 24 with a gap while an outer circumferential surface 30c of the light projecting lens 30 is not basically in contact with a circumferential surface of the light projecting lens inserting hole 24. At this point, the light projecting lens 30 is sandwiched between the blocking unit 23 and the light projecting fiber 10 in the axial direction, so that the light projecting lens 30 is fixed to the case body 20.

Therefore, the light projecting lens 30 is fixed while pressed against the blocking unit 23 of the case body 20 by the light projecting fiber 10, and an optical axis of the light projecting fiber 10 and an optical center of the light projecting lens 30 are substantially located on an identical straight line after the light projecting lens 30 is fixed.

As illustrated in FIG. 2, in the optical fiber head 1A of the first embodiment, a diameter $R_{A1}$ in the leading end portion of the light projecting fiber 10 is larger than a diameter $R_{A2}$ of the light projecting lens 30 ($R_{A1} > R_{A2}$).

Under the above condition, an inner diameter $R_{A3}$ of the light projecting fiber inserting hole 25 is slightly larger than the diameter $R_{A1}$ in the leading end portion of the light projecting fiber 10 ($R_{A3} > R_{A0}$ such that the light projecting fiber 10 can be inserted in the light projecting fiber inserting hole 25 as illustrated in FIG. 4, and an inner diameter $R_{A4}$ of the light projecting lens inserting hole 24 is slightly larger than the diameter $R_{A2}$ of the light projecting lens 30 ($R_{A4} > R_{A2}$) such that the light projecting lens 30 can be inserted in the light projecting lens inserting hole 24 as illustrated in FIG. 3.

Under the above conditions, an diameter $R_{A5}$ of the light projecting opening 23a is smaller than the diameter $R_{A2}$ of the light projecting lens 30 ($R_{A5} < R_{A2}$) such that a circumferential edge of the light projecting lens 30 abuts on the blocking unit 23 while the light projecting lens 30 is inserted in the light projecting lens inserting hole 24 as illustrated in FIG. 3.

Under the above conditions, a length $L_{A1}$ in the axial direction of the light projecting lens 30 is longer than a length $L_{A2}$ in the axial direction of the light projecting lens inserting hole 24 ($L_{A1} > L_{A2}$) such that the rear end of the light projecting lens 30 is located in the light projecting fiber inserting hole 25 while the light projecting lens 30 is inserted in the light projecting lens inserting hole 24 as illustrated in FIG. 2.

The light projecting lens 30 is sandwiched between the blocking unit 23 and the light projecting fiber 10 in the axial direction as described above by satisfying the above conditions, and the light projecting lens 30 can be fixed to the case body 20.

At this point, as illustrated in FIG. 2, the crimping portion 22a is provided at a position on the rear end side of the case body 20 while separated from the portion in which the leading end surface 10a of the light projecting fiber 10 is located in the axial direction of the case body 20. With this configuration, an influence of elongation of the light projecting fiber 10 in the axial direction of the case body 20, which is caused by the crimping of the light projecting fiber 10 using the crimping portion 22a, on the leading end surface 10a of the light projecting fiber 10 can be relaxed to accurately perform the positioning of the leading end surface 10a of the light projecting fiber 10.

Figure 6:
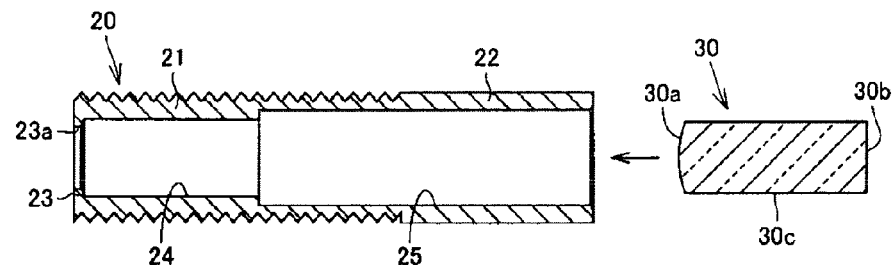
FIG. 6 is a schematic diagram illustrating a procedure to assemble the optical fiber head of the first embodiment of the present invention.
Figure 7:
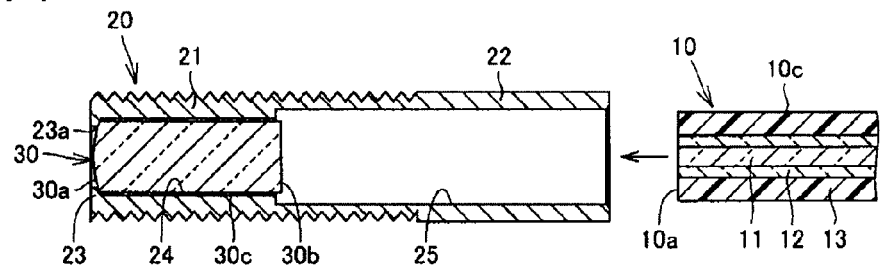
FIG. 7 is a schematic diagram illustrating the procedure to assemble the optical fiber head of the first embodiment of the present invention.
Figure 8:
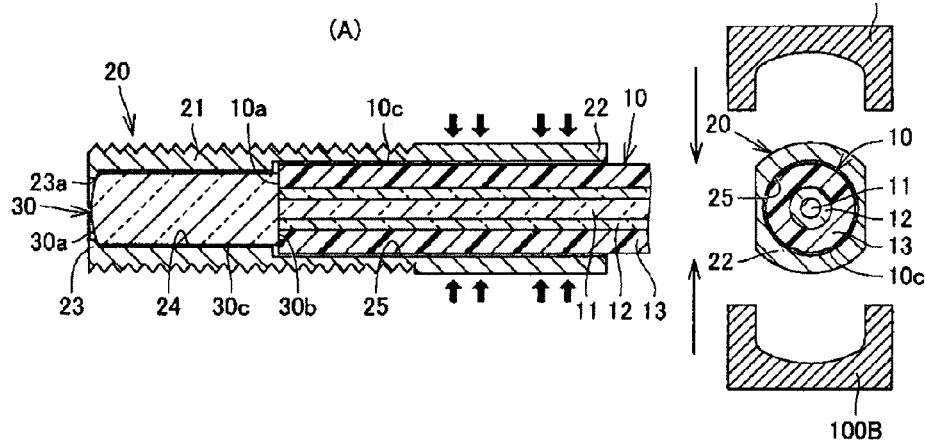
FIGS. 8A and 8B are schematic diagrams illustrating the procedure to assemble the optical fiber head of the first embodiment of the present invention.

FIGS. 6 to 8 are schematic diagrams illustrating a procedure to assemble the optical fiber head of the first embodiment. The procedure to assemble the optical fiber head 1A of the first embodiment will be described below with reference to FIGS. 6 to 8.

In assembling the optical fiber head 1A of the first embodiment, at first the light projecting lens 30 is inserted in the case body 20 as illustrated in FIG. 6. At this point, the light projecting lens 30 is inserted from the rear end side of the case body 20 so as to reach the light projecting lens inserting hole 24 through the light projecting fiber inserting hole 25 made in the case body 20, and the front end surface 30a of the light projecting lens 30 abuts on the blocking unit 23 of the case body 20. At this point, a convex lens portion provided in the front end surface 30a of the light projecting lens 30 is fitted in the light projecting opening 23a provided in the blocking unit 23, thereby positioning the light projecting lens 30 with respect to the case body 20.

Then, as illustrated in FIG. 7, the leading end portion of the light projecting fiber 10 is inserted in the case body 20 in which the light projecting lens 30 is inserted. At this point, the leading end portion of the light projecting fiber 10 is inserted into the light projecting fiber inserting hole 25 made in the case body 20 from the rear end side of the case body 20. At this point, the leading end surface 10a of the light projecting fiber 10 abuts on the rear end surface 30b of the light projecting lens 30 previously inserted in the case body 20. In the leading end portion of the light projecting fiber 10, because the core wire may remain coated with the coating material 13, it is not necessary to remove the coating material 13 to expose the core wire.

Then, as illustrated in FIGS. 8A and 8B, the crimping is performed to the fixing unit 22 of the case body 20 using crimping tools 100A and 100B having predetermined shapes. For example, as illustrated in FIG. 8B, halved tools are used as the crimping tools 100A and 100B. The crimping tools 100A and 100B are disposed so as to nip the fixing unit 22, and the crimping is performed by bringing the crimping tools 100A and 100B close to each other.

The fixing unit 22 is plastically deformed such that the diameter of part of the fixing unit 22 is reduced, thereby forming the crimping portion 22a in the fixing unit 22. Therefore, the leading end portion of the light projecting fiber 10 is fixed to the case body 20.

The assembly of the optical fiber head 1A of the first embodiment is completed through the above processes, and the optical fiber head 1A having the configuration in FIGS. 1 to 5 is produced.

As described above, in the optical fiber head 1A of the first embodiment, the light projecting lens 30 can be fixed to the case body 20 by the simple configuration, and therefore the optical fiber head can easily be produced at low cost.

That is, in the optical fiber head 1A of the first embodiment, it is not necessary to strictly manage dimension accuracy of the light projecting lens or the case body more than necessary compared with the case that the light projecting lens is fixed to the case body by the press-fitting, and it is not necessary to perform work to apply and cure a bonding agent compared with the light projecting lens is fixed to the case body using the bonding agent. As a result, the production cost can largely be reduced.

In the optical fiber head 1A of the first embodiment, because a stress is not applied to the outer circumferential surface of the light projecting lens compared with the case that the light projecting lens is fixed to the case body by the press-fitting, advantageously there is no risk of generating an adverse effect on the optical property.

In the optical fiber head 1A of the first embodiment, the necessity of the bonding agent is eliminated compared with the light projecting lens is fixed to the case body using the bonding agent. Therefore, the optical fiber head 1A can be mounted in a high-temperature environment, where the optical fiber head in which the bonding agent is used is difficult to mount due to a low heat-resistant property, and the optical fiber head 1A can be mounted in a clean environment of a semiconductor production site where the optical fiber head in which the bonding agent is used is difficult to mount due to generation of outgas from the bonding agent. As a result, advantageously an application range of the optical fiber head can largely be expanded.

In the first embodiment, by way of example, the diameter $R_{A1}$ in the leading end portion of the light projecting fiber 10 is larger than the diameter $R_{A2}$ of the light projecting lens 30. Alternatively, the diameter $R_{A1}$ in the leading end portion of the light projecting fiber 10 may be smaller than or equal to the diameter $R_{A2}$ of the light projecting lens 30.

In the first embodiment, by way of example, the light projecting fiber 10 is fixed to the case body 20 by the crimping. Alternatively, the light projecting fiber 10 may be fixed to the case body 20 by the use of a crimping ring or the bonding. However, in the case that the light projecting fiber 10 is fixed to the case body 20 by the bonding, sometimes there is a restriction to the light projecting fiber 10 mounted in the clean environment.

In the first embodiment, by way of example, the present invention is applied to the light projecting head of the transmission optical fiber type photoelectric sensor. The present invention can also be applied to the light receiving head of the transmission optical fiber type photoelectric sensor.

Second Embodiment

Figure 9:
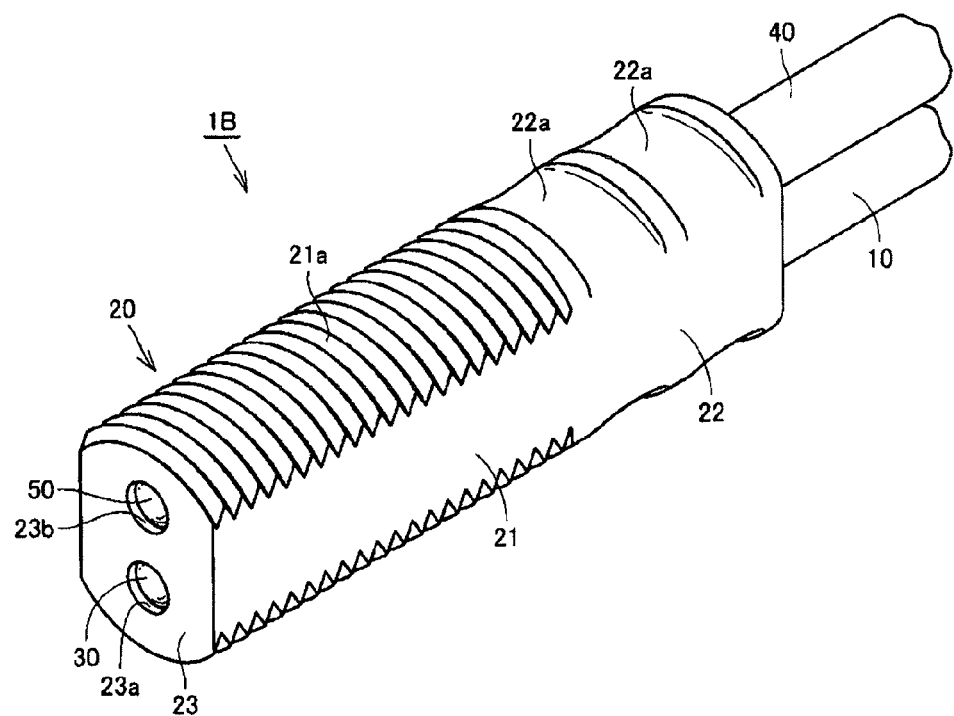
FIG. 9 is a perspective view of an optical fiber head according to a second embodiment of the present invention.
Figure 10:
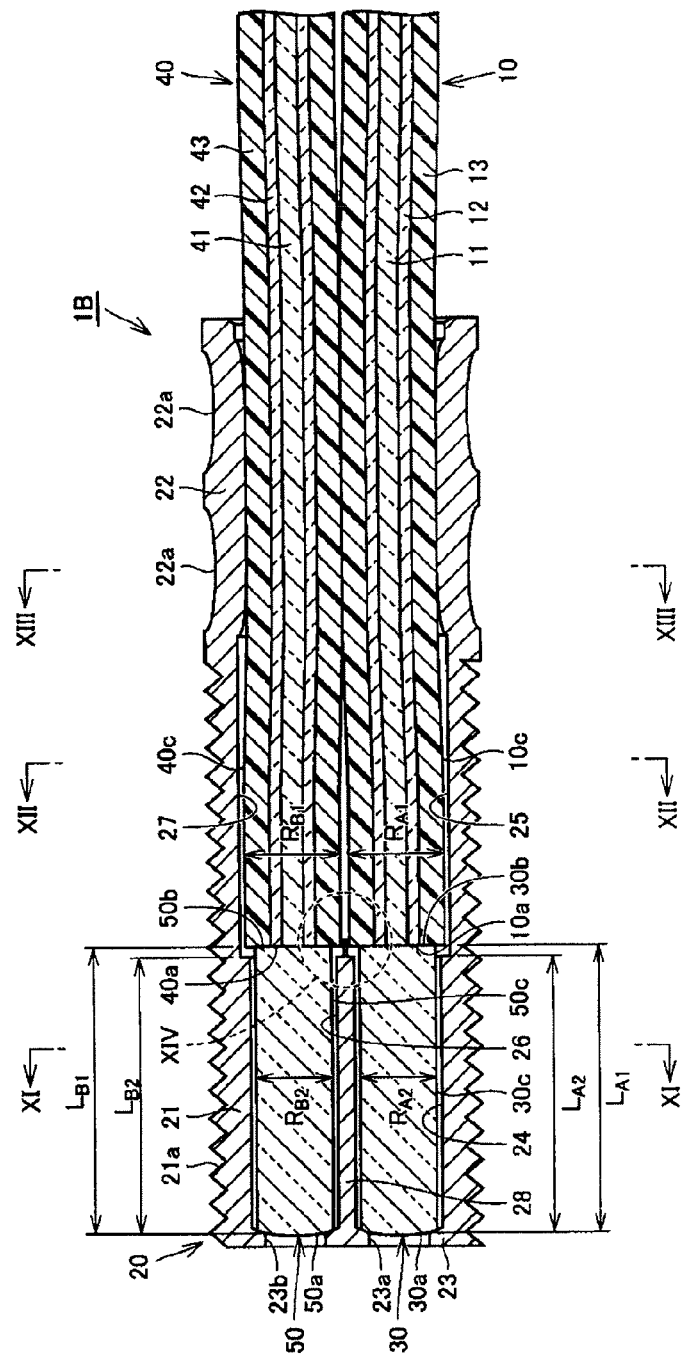
FIG. 10 is a sectional view of the optical fiber head in FIG. 9.
Figure 11:
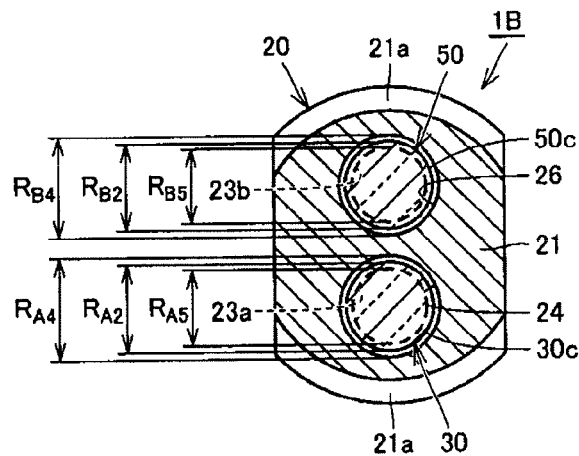
FIG. 11 is a sectional view taken along line XI-XI of FIG. 10.
Figure 12:
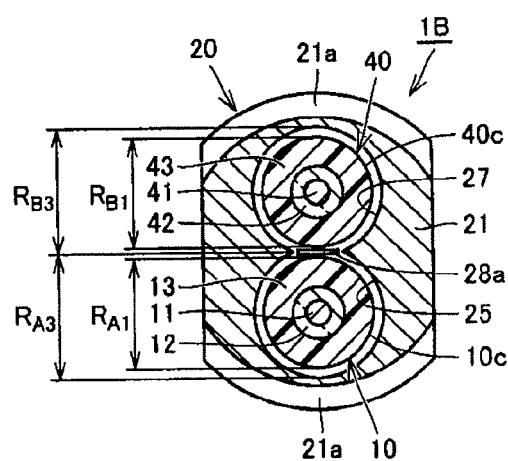
FIG. 12 is a sectional view taken along line XII-XII of FIG. 10.
Figure 13:
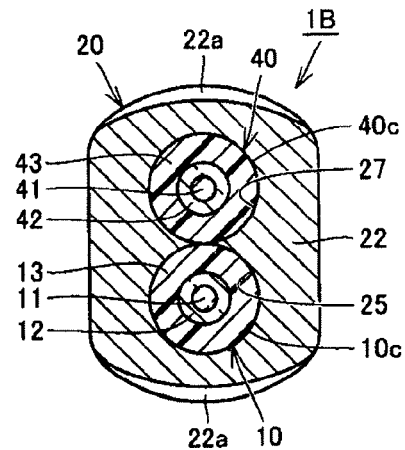
FIG. 13 is a sectional view taken along line XIII-XIII of FIG. 10.
Figure 14:
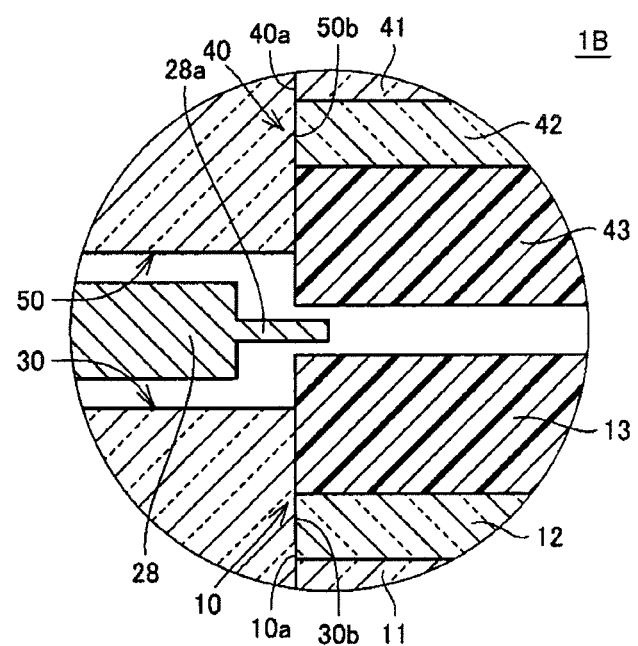
FIG. 14 is an enlarged sectional view illustrating a region XIV of the optical fiber head in FIG. 10.

FIG. 9 is a perspective view of an optical fiber head according to a second embodiment of the present invention, and FIG. 10 is a sectional view of the optical fiber head in FIG. 9. FIGS. 11 to 13 are sectional views taken along lines XI-XI, XII-XII, and XIII-XIII of FIG. 10, respectively. FIG. 14 is an enlarged sectional view illustrating a region XIV of the optical fiber head in FIG. 10. A configuration of an optical fiber head 1B of the second embodiment will be described below with reference to FIGS. 9 to 14. The optical fiber head 1B of the second embodiment is configured as a light projecting and receiving head of a reflection optical fiber type photoelectric sensor.

As illustrated in FIGS. 9 to 13, the optical fiber head 1B of the second embodiment includes the light projecting fiber 10, a light receiving fiber 40, the case body 20, the light projecting lens 30, and a light receiving lens 50. In the optical fiber head 1B, in addition to the light projecting fiber 10 and the light projecting lens 30, the light receiving fiber 40 and the light receiving lens 50 are assembled in the case body 20 of the optical fiber head 1A of the first embodiment. For this reason, the shapes of the light projecting fiber 10 and the light projecting lens 30 and the structure in which the light projecting fiber 10 and the light projecting lens 30 are assembled in the case body 20 are basically similar to those of the first embodiment.

The light receiving fiber 40 transmits the light and projects the light toward the outside, and the light receiving fiber 40 is made of the material identical to that of the light projecting fiber 10. The light receiving fiber 40 includes a leading end surface 40a on which the light is incident, and includes a core 41, a clad 42, and a coating material 43. In the leading end portion of the light receiving fiber 40, the core wire including the core 41 and the clad 42 is not exposed, but the core wire is coated with the coating material 43.

The light receiving lens 50 controls the ray of the light incident from the outside and causes the light to be incident on the light receiving fiber 40. The light receiving lens 50 is made of the material identical to that of the light projecting lens 30. A front end surface 50a (the left end surface in FIG. 10) of the light receiving lens 50 is configured by a convex lens surface, and a rear end surface 50b (the right end surface in FIG. 10) is configured by a planar surface.

In addition to the light projecting lens inserting hole 24, a light receiving lens inserting hole 26 in which the light receiving lens 50 is inserted is made in the case body 20 on the front end side of the main body 21. In addition to the light projecting fiber inserting hole 25, a light receiving fiber inserting hole 27 in which the leading end portion of the light receiving fiber 40 is inserted is made in the main body 21 on the rear end side and in the fixing unit 22. In addition to the light projecting opening 23a, a light receiving opening 23b is provided in the blocking unit 23 so as to pierce the blocking unit 23 in the axial direction. The light receiving opening 23b causes the light exiting toward the optical fiber head 1B to be incident on the light receiving lens 50.

The light receiving opening 23b, the light receiving lens inserting hole 26, and the light receiving fiber inserting hole 27 pierce the case body 20 so as to communicate with one another. Therefore, the blocking unit 23 in which the light receiving opening 23b is provided, the light receiving lens inserting hole 26 in which the light receiving lens 50 is inserted, and the light receiving fiber inserting hole 27 in which the leading end portion of the light receiving fiber 40 is inserted are sequentially provided in the case body 20 from the front end to the rear end.

At this point, the light projecting lens inserting hole 24 and the light receiving lens inserting hole 26 are partitioned by a partition 28 provided in the case body 20. On the other hand, the light projecting fiber inserting hole 25 and the light receiving fiber inserting hole 27 are not substantially partitioned, but communicate with each other.

The leading end portion of the light receiving fiber 40 and the light receiving lens 50 are accommodated in the light receiving fiber inserting hole 27 and the light receiving lens inserting hole 26, which are provided in the case body 20, respectively. More particularly, the leading end portion of the light receiving fiber 40 is disposed in the light receiving fiber inserting hole 27 made on the rear end side of the case body 20, and the light receiving lens 50 is mainly disposed in the light receiving lens inserting hole 26 made on the front end side of the case body 20. A portion except the leading end portion of the light receiving fiber 40 is externally drawn from the rear end of the case body 20.

Therefore, the leading end surface 40a of the light receiving fiber 40 and the rear end surface 50b of the light receiving lens 50 are disposed in the case body 20 while opposed to each other, and the leading end surface 40a of the light receiving fiber 40 and the rear end surface 50b of the light receiving lens 50 abut on each other in the case body 20.

The leading end portion of the light projecting fiber 10 and the leading end portion of the light receiving fiber 40 are integrally held by the crimping portion 22a provided in the fixing unit 22 of the case body 20. The fixing unit 22 is plastically deformed such that the diameter of part of the fixing unit 22 is reduced in the axial direction, thereby forming the crimping portion 22a. The leading end portion of the light projecting fiber 10 and the leading end portion of the light receiving fiber 40 are bundled by the crimping portion 22a. At this point, the crimping portion 22a bites into both the outer circumferential surface 10c of the light projecting fiber 10 and an outer circumferential surface 40c of the light receiving fiber 40 to integrally hold the leading end portion of the light projecting fiber 10 and the leading end portion of the light receiving fiber 40.

On the other hand, similarly to the light projecting lens 30, the light receiving lens 50 is sandwiched between the blocking unit 23 of the case body 20 and the light receiving fiber 40 in the axial direction, so that the light receiving lens 50 is fixed to the case body 20. That is, the light receiving lens 50 is not press-fitted in the light receiving lens inserting hole 26, but the light receiving lens 50 is disposed in the light receiving lens inserting hole 26 with a gap while an outer circumferential surface 50c of the light receiving lens 50 is not basically in contact with a circumferential surface of the light receiving lens inserting hole 26. At this point, the light receiving lens 50 is sandwiched between the blocking unit 23 and the light receiving fiber 40 in the axial direction, so that the light receiving lens 50 is fixed to the case body 20.

Therefore, similarly to the light projecting lens 30, the light receiving lens 50 is fixed while pressed against the blocking unit 23 of the case body 20 by the light receiving fiber 40, and the optical axis of the light receiving fiber 40 and the optical center of the light receiving lens 50 are substantially located on the identical straight line after the light receiving lens 50 is fixed.

As illustrated in FIG. 10, in the optical fiber head 1B of the second embodiment, a diameter $R_{B1}$ in the leading end portion of the light receiving fiber 40 is larger than a diameter $R_{B2}$ of the light receiving lens 50 ($R_{B1} > R_{B2}$).

Under the above condition, an inner diameter $R_{B3}$ of the light receiving fiber inserting hole 27 is slightly larger than the diameter $R_{B1}$ in the leading end portion of the light receiving fiber 40 ($R_{B3} > R_{B1}$) such that the light receiving fiber 40 can be inserted in the light receiving fiber inserting hole 27 as illustrated in FIG. 12, and an inner diameter $R_{B4}$ of the light receiving lens inserting hole 26 is slightly larger than the diameter $R_{B2}$ of the light receiving lens 50 ($R_{B4} > R_{B2}$) such that the light receiving lens 50 can be inserted in the light receiving lens inserting hole 26 as illustrated in FIG. 11.

Under the above conditions, an diameter $R_{B5}$ of the light receiving opening 23b is smaller than the diameter $R_{B2}$ of the light receiving lens 50 ($R_{B5} < R_{B2}$) such that the circumferential edge of the light receiving lens 50 abuts on the blocking unit 23 while the light receiving lens 50 is inserted in the light receiving lens inserting hole 26 as illustrated in FIG. 11.

Under the above conditions, a length $L_{B1}$ in the axial direction of the light receiving lens 50 is longer than a length $L_{B2}$ in the axial direction of the light receiving lens inserting hole 26 ($L_{B1}>L_{B2}$) such that the rear end of the light receiving lens 50 is located in the light receiving fiber inserting hole 27 while the light receiving lens 50 is inserted in the light receiving lens inserting hole 26 as illustrated in FIG. 10.

The light receiving lens 50 is sandwiched between the blocking unit 23 and the light receiving fiber 40 in the axial direction as described above by satisfying the above conditions, and the light receiving lens 50 can be fixed to the case body 20.

Because the procedure to assemble the optical fiber head 1B of the second embodiment is similar to that of the optical fiber head 1A of the first embodiment, the description thereof is not given here.

As described above, in the optical fiber head 1B of the second embodiment, similarly to the first embodiment, the light projecting lens 30 and the light receiving lens 50 can be fixed to the case body 20 by the simple configuration, and therefore the optical fiber head can easily be produced at low cost.

That is, in the optical fiber head 1B of the second embodiment, it is not necessary to strictly manage dimension accuracy of the light projecting lens, the light receiving lens, or the case body more than necessary compared with the case that the light projecting lens and the light receiving lens are fixed to the case body by the press-fitting, and it is not necessary to perform work to apply and cure the bonding agent compared with the light projecting lens and the light receiving lens are fixed to the case body using the bonding agent. As a result, the production cost can largely be reduced.

As illustrated in FIG. 14, in the optical fiber head 1B of the second embodiment, a partition wall 28a projects from the rear end surface of the partition 28 provided in the case body 20 so as to reach a gap between the light projecting fiber 10 and the light receiving fiber 40. The partition wall 28a is provided in order to prevent generation of what is called a crosstalk (a phenomenon in which part of the light exiting from the light projecting fiber reaches the light receiving fiber through not the outside of the optical fiber head but the inside of the optical fiber head).

In the optical fiber head 1B of the second embodiment, the length $L_{A1}$ in the axial direction of the light projecting lens 30 is longer than the length $L_{A2}$ in the axial direction of the light projecting lens inserting hole 24, and the length $L_{B1}$ in the axial direction of the light receiving lens 50 is longer than the length $L_{B2}$ in the axial direction of the light receiving lens inserting hole 26. Therefore, in the case that the partition wall 28a is not provided, the rear ends of the light projecting lens 30 and the light receiving lens 50 are opposed to each other with no obstruction interposed therebetween at the front ends of the light projecting fiber inserting hole 25 and the light receiving fiber inserting hole 27, and the crosstalk is possibly generated.

When the partition wall 28a is provided in the partition 28 as described above, the rear ends of the light projecting lens 30 and the light receiving lens 50 are obstructed by the partition wall 28a at the front ends of the light projecting fiber inserting hole 25 and the light receiving fiber inserting hole 27, and the generation of the crosstalk can be prevented before happens.

In the second embodiment, by way of example, the diameter $R_{A1}$ in the leading end portion of the light projecting fiber 10 is larger than the diameter $R_{A2}$ of the light projecting lens 30, and the diameter $R_{B1}$ in the leading end portion of the light receiving fiber 40 is larger than the diameter $R_{B2}$ of the light receiving lens 50. Alternatively, the diameter $R_{A1}$ in the leading end portion of the light projecting fiber 10 may be smaller than or equal to the diameter $R_{A2}$ of the light projecting lens 30, and the diameter $R_{B1}$ in the leading end portion of the light receiving fiber 40 may be smaller than or equal to the diameter $R_{B2}$ of the light receiving lens 50.

In the second embodiment, by way of example, the light projecting fiber 10 and the light receiving fiber 40 are fixed to the case body 20 by the crimping. Alternatively, the light projecting fiber 10 and the light receiving fiber 40 may be fixed to the case body 20 by various methods such as the use of the crimping ring and the bonding.

In the second embodiment, by way of example, the light projecting fiber inserting hole 25 and the light receiving fiber inserting hole 27 communicate with each other in the case body 20. Alternatively, the light projecting fiber inserting hole 25 and the light receiving fiber inserting hole 27 may be partitioned by providing the partition in the case body 20.

In the first and second embodiments, by way of example, the present invention is applied to the optical fiber head in which the external thread is formed on the outer circumferential surface of the case body. However, the external thread is not necessarily formed. The present invention may be applied to the optical fiber head in which the external thread is not provided.

The embodiments are disclosed only by way of example, but are not restrictive. The technical scope of the present invention is defined by the claims, and the meanings equivalent to the claims and all the changes within the technical scope are also included in the present invention.

What is claimed is:

1. An optical fiber head comprising:
an elongated, columnar optical fiber comprising a leading end surface in a leading end portion in an axial direction, light exiting from and being incident on the leading end surface;
a substantially columnar lens disposed so as to be opposed to the leading end surface of the optical fiber; and
a case body comprising a front end and a rear end in the axial direction, the leading end portion of the optical fiber and the lens being accommodated in the case body, the optical fiber being drawn from the rear end of the case body,
wherein
a blocking unit, a lens inserting hole, and an optical fiber inserting hole are sequentially provided in the case body from the front end to the rear end, an opening through which the light is projected or received being formed in the blocking unit, the lens being inserted in the lens inserting hole, the leading end portion of the optical fiber being inserted in the optical fiber inserting hole,
an inner diameter of the lens inserting hole is larger than a diameter of the opening and is smaller than an inner diameter of the optical fiber inserting hole,
a length in the axial direction of the lens is longer than a length in the axial direction of the lens inserting hole, and
the leading end portion of the optical fiber is fixed to the case body while the leading end surface of the optical fiber abuts on a rear end surface of the lens by inserting the lens in the lens inserting hole, and the leading end portion of the optical fiber in the optical fiber inserting hole, so that the lens is fixed to the case body by being sandwiched between the blocking unit and the optical fiber in the axial direction.

2. The optical fiber head according to claim 1, wherein a diameter in the leading end portion of the optical fiber is larger than a diameter of the lens.

3. The optical fiber head according to claim 1, wherein the leading end portion of the optical fiber comprises:

a core wire comprising a core and a clad; and
a coating material coating the core wire.

4. The optical fiber head according to claim 3, wherein the leading end portion of the optical fiber is fixed to the case body by crimping in which a diameter of a part of the case body is radially reduced.

5. An optical fiber head comprising:
an elongated, columnar light projecting fiber comprising a leading end surface in a leading end portion in an axial direction, light exiting from the leading end surface;
an elongated, columnar light receiving fiber comprising a leading end surface in a leading end portion in an axial direction, the light being incident on the leading end surface;
a substantially columnar light projecting lens disposed so as to be opposed to the leading end surface of the light projecting fiber;
a substantially columnar light receiving lens disposed so as to be opposed to the leading end surface of the light receiving fiber; and
a case body comprising a front end and a rear end in the axial direction, the leading end portion of the light projecting fiber, the leading end portion of the light receiving fiber, the light projecting lens, and the light receiving lens being accommodated in the case body, the light projecting fiber and the light receiving fiber being drawn from the rear end of the case body,
wherein
a blocking unit, lens inserting holes, and optical fiber inserting holes are sequentially provided in the case body from the front end to the rear end, a light projecting opening through which the light is projected and a light receiving opening through which the light is received being formed in the blocking unit, the light projecting lens and the light receiving lens being inserted in the lens inserting holes, the leading end portion of the light projecting fiber and the leading end portion of the light receiving fiber being inserted in the optical fiber inserting hole,
the case body comprises a partition configured to partition a light projecting lens inserting hole and a light receiving lens inserting hole of the lens inserting holes, the light projecting lens being inserted in light projecting lens inserting hole, the light receiving lens being inserted in the light receiving lens inserting hole,
an inner diameter of the light projecting lens inserting hole is larger than a diameter of the light projecting opening, and is smaller than an inner diameter of the light projecting fiber inserting hole, which is a hole in which the light projecting fiber is inserted in the optical fiber inserting holes,
an inner diameter of the light receiving lens inserting hole is larger than a diameter of the light receiving opening, and is smaller than an inner diameter of the light receiving fiber inserting hole, which is a hole in which the light receiving fiber is inserted in the optical fiber inserting holes,
a length in the axial direction of the light projecting lens is longer than a length in the axial direction of the light projecting lens inserting hole,
a length in the axial direction of the light receiving lens is longer than a length in the axial direction of the light receiving lens inserting hole, and
the leading end portion of the light projecting fiber and the leading end portion of the light receiving fiber are fixed to the case body while the leading end surface of the light projecting fiber and the leading end surface of the light receiving fiber respectively abut on a rear end surface of the light projecting lens and a rear end surface of the light receiving lens by inserting the light projecting lens in the light projecting lens inserting hole, the leading end portion of the light projecting fiber in the light projecting fiber inserting hole, the light receiving lens in the light receiving lens inserting hole, and the leading end portion of the light receiving fiber in the light receiving fiber inserting hole, so that the light projecting lens is sandwiched between the blocking unit and the light projecting fiber in the axial direction and the light receiving lens is sandwiched between the blocking unit and the light receiving fiber in the axial direction, and the light projecting lens and the light receiving lens are fixed to the case body.

6. The optical fiber head according to claim 5, wherein
a diameter in the leading end portion of the light projecting fiber is larger than a diameter of the light projecting lens, and
a diameter in the leading end portion of the light receiving fiber is larger than a diameter of the light receiving lens.

7. The optical fiber head according to claim 5, wherein each of the leading end portions of the light projecting fiber and the light receiving fiber comprises:
a core wire comprising a core and a clad; and
a coating material coating the core wire.

8. The optical fiber head according to claim 7, wherein
a partition wall projects from the rear end surface of the partition so as to reach a gap between the light projecting fiber and the light receiving fiber.

9. The optical fiber head according to claim 7, wherein the leading end portion of the light projecting fiber and the leading end portion of the light receiving fiber are fixed to the case body by crimping in which a diameter of part of the case body is radially reduced.

10. The optical fiber head according to claim 2, wherein the leading end portion of the optical fiber comprises:
a core wire comprising a core and a clad; and
a coating material coating the core wire.

11. The optical fiber head according to claim 6, wherein each of the leading end portions of the light projecting fiber and the light receiving fiber comprises:
a core wire comprising a core and a clad; and
a coating material coating the core wire.

12. The optical fiber head according to claim 8, wherein the leading end portion of the light projecting fiber and the leading end portion of the light receiving fiber are fixed to the case body by crimping in which a diameter of part of the case body is radially reduced.

* * * * *